United States Patent [19]

Habeck et al.

[11] 3,932,430
[45] *Jan. 13, 1976

[54] SUBSTITUTED INDENO, NAPHTHO AND CYCLOHEPTA PYRAZOLES

[75] Inventors: Dietmar A. Habeck, Heidelberg, Germany; William J. Houlihan, Mountain Lakes, N.J.

[73] Assignee: Sandoz, Inc., E. Hanover, N.J.

[ * ] Notice: The portion of the term of this patent subsequent to Oct. 15, 1991, has been disclaimed.

[22] Filed: Apr. 11, 1973

[21] Appl. No.: 350,140

Related U.S. Application Data

[63] Continuation-in-part of Ser. No. 341,392, March 15, 1973, abandoned, which is a continuation-in-part of Ser. No. 302,595, Oct. 31, 1972, abandoned, which is a continuation-in-part of Ser. No. 289,155, Sept. 14, 1972, abandoned, which is a continuation-in-part of Ser. No. 231,387, March 2, 1972, abandoned, which is a continuation-in-part of Ser. No. 259,859, June 5, 1972, abandoned, which is a continuation-in-part of Ser. No. 274,868, July 25, 1972, abandoned, which is a continuation-in-part of Ser. No. 188,938, Oct. 13, 1971, abandoned.

[52] U.S. Cl.... 260/296 T; 260/294.8 R; 260/295 S; 260/296 B; 260/296 P; 260/310 R; 260/240 R; 424/263; 424/273
[51] Int. Cl.$^2$.................................... C07D 213/74
[58] Field of Search...... 260/296 T, 296 P, 294.8 R, 260/295 S

[56] References Cited
UNITED STATES PATENTS

| | | | |
|---|---|---|---|
| 3,816,438 | 6/1974 | Houlihan | 260/294.8 B |
| 3,843,664 | 10/1974 | Habeck et al. | 260/296 T |

Primary Examiner—Alan L. Rotman
Attorney, Agent, or Firm—Gerald D. Sharkin; Robert S. Honor; Thomas O. McGovern

[57] ABSTRACT

Substituted indeno [1,2-c] pyrazoles, naphtho [1,2-c] pyrazoles and benzo [6,7] cyclohepta [1,2-c] pyrazoles e.g., 3-(2,3-dimethoxyphenyl)-4H-indeno[1,2-c] pyrazole and 4,5-dihydro-3-(4-pyridyl)-2H-naphtho[1,2-c] pyrazole, are useful as non-estrogenic anti-fertility agents and antihypertensive agents.

9 Claims, No Drawings

SUBSTITUTED INDENO, NAPHTHO AND CYCLOHEPTA PYRAZOLES

This is a continuation-in-part of copending U.S. Pat. application serial No. 341,392 filed Mar. 15, 1973, now abandoned which in turn is a continuation-in-part of copending U.S. Pat. application serial No. 305,595, filed Oct. 31, 1972, now abandoned which in turn is a continuation-in-part of copending U.S. Pat. application serial No. 289,155 filed Sept. 14, 1972, now abandoned which in turn is a continuation-in-part of copending applications Ser. No. 231,387, filed Mar. 2, 1972; now abandoned, Ser. No. 259,859, filed June 5, 1972, now abandoned and Ser. No. 274,868, filed July 25, 1972, now abandoned which in turn are continuations-in-part of copending application Ser. No. 188,938, filed Oct. 13, 1971, now abandoned.

This invention relates to indeno [1,2-c] pyrazole, naphtho [1,2-c] pyrazole and benzo [6,7] cyclohepta [1,2-c] pyrazole. More particularly it relates to 3-aryl and 3-heterocyclic derivatives of indeno [1,2-c] pyrazole, naphtho [1,2-c] pyrazole and benzo [6,7] cyclohepta [1,2-c] pyrazole and their use in pharmaceutical compositions.

The compounds of this invention may be represented by the following formula:

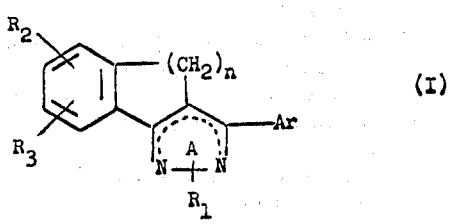

where
$n$ is 1, 2 or 3
$R_1$ represents hydrogen or lower alkyl having 1 to 4 carbon atoms but excluding tertiary butyl, e.g., methyl, ethyl, isopropyl, and the like:
Ar is

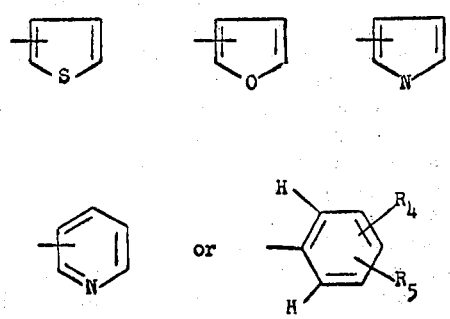

and
$R_2$, $R_3$, $R_4$ and $R_5$ each independently represent hydrogen, halo having an atomic weight of about 19 to 36, lower alkyl, ie. alkyl having 1 to 4 carbon atoms, e.g. methyl, ethyl, isopropyl and the like; lower alkoxy, i.e., alkoxy having 1 to 4 carbon atoms, e.g., methoxy, ethoxy, isopropoxy, and the like, or trifluoromethyl, or $R_2$ and $R_3$ or $R_4$ and $R_5$ together independently represent methylenedioxy attached to adjacent carbon atoms provided that when $R_2$ and $R_3$ or $R_4$ and $R_5$ are independently trifluoromethyl or tertiary butyl, they are not on adjacent carbon atoms; and when n is 1 and $R_1$, $R_2$ and $R_3$ are hydrogen, Ar is other than unsubstituted phenyl and pharmaceutically acceptable acid addition salts thereof.

The pyrazole ring (A) in the compounds of formula (I) can have the following structures:

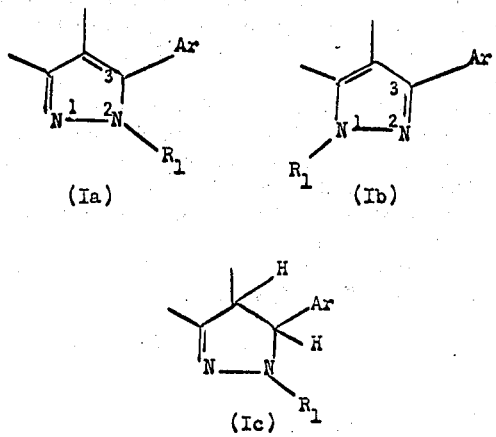

where $R_1$ is as defined above. It should be noted that when $R_1$ is hydrogen the compounds of structures (Ia) and Ib) are considered equivalent and are known to exist in both tautomeric forms. It should also be noted that this invention includes the geometrical and optical isomers of the compounds of structures (c).

The compounds of formula (I) in which ring A has the structure (Ia) and (Ib) may be prepared by the following reaction scheme:

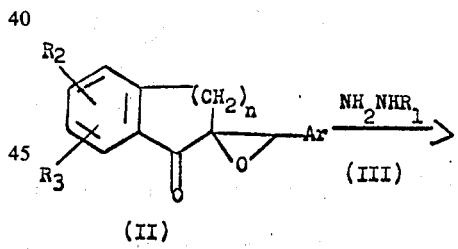

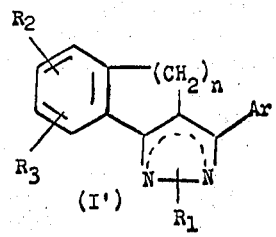

where $n$, $R_1$, $R_2$, $R_3$, Ar and the proviso are as defined above.

The compounds of formula (I') are prepared by treating a compound of formula (II) with a compound of formula (III). The reaction is preferably carried out under acidic catalysis which can be provided by a mineral acid such as hydrochloric acid, sulfuric acid, and the like, a strong organic acid such as acetic acid or p-toluenesulfonic acid or a Lewis acid such as boron trifluoride. The preferred acid is acetic acid. Although a solvent is not required, it is preferred that the reaction be carried out in the presence of an inert solvent such as the lower alkanols, aliphatic or aromatic hydrocarbons, halogenated hydrocarbons, straight chain ethers or cyclic ethers. The particular solvent used is not critical, but the lower alkanols, such as methanol, ethanol, butanol and the like or dioxane are preferred, especially ethanol and dioxane. The temperature of the reaction also is not critical, but it is generally carried out between 35° and 200°C, preferably at the reflux temperature of the system. For optimum results it is preferred that the reaction be run for from 8 hours to 5 days. The product is recovered in the usual manner, e.g., by evaporation and crystallization. The compounds of formula (II) can exist in the form of cis and trans isomers. It is not critical which isomer is used in the process; and although the trans form reacts faster than the cis form, a mixture of the two isomers is generally used in the reaction.

The compounds of formula (Ic) can also be prepared by the following reaction scheme:

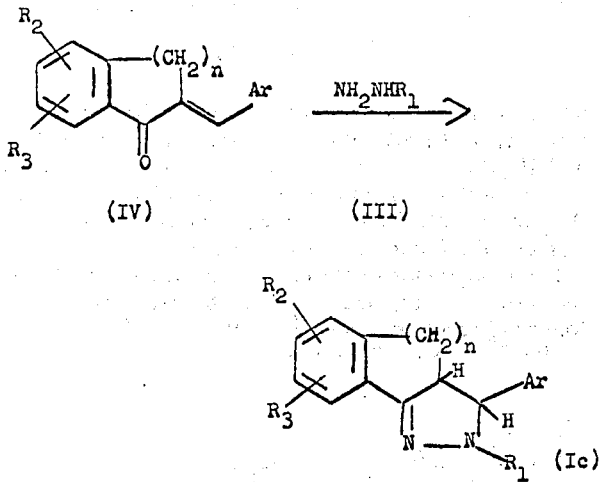

where $n$, $R_1$, $R_2$, $R_3$, Ar and the proviso are as set out above.

The compounds of formula (Ic) are prepared by treating a compound of formula (IV) with a compound of formula (III). Although a solvent is not necessary, it is preferred that the reaction be carried out in an inert solvent, e.g., the above lower alkanols, aliphatic or aromatic hydrocarbons, halogenated hydrocarbons, straight chain ethers or cyclic ethers. The particular solvent used is not critical but the preferred solvents are the lower alkanols such as methanol, ethanol, butanol and the like. The temperature of the reaction is not critical, but it is normally carried out between 35° and 150°C, preferably at the reflux temperature of the system. For optimum results, it is preferred that the reaction be run for from 8 hours to 5 days under anhydrous conditions. When the preceeding reaction is carried out in an inert atmosphere, such as helium, argon or nitrogen, the compound with structure (Ic) is predominantly obtained and is isolated by conventional techniques, e.g., chromatography. The compounds of formula (IV) can also exist in cis and trans form. It is not critical which isomer is used in the reaction; and although the trans form reacts faster than the cis form, a mixture of the two isomers is generally used in the reaction.

The compounds of formula (I') in which $R_1$ is hydrogen may also be prepared in accordance with the following reaction scheme:

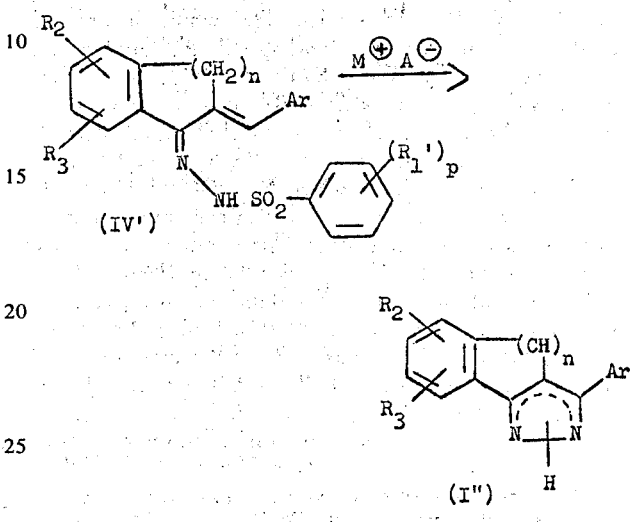

where
$p$ is 0, 1 or 2
$R_1'$ is lower alkyl having 1 to 3 carbon atoms, e.g., methyl, ethyl, isopropyl and the like;
$M^+A^-$ is a non-hydroxyl anionic cyclizing agent and $n$, Ar, $R_2$, $R_3$ and the proviso are as defined previously.

The compounds of formula (I'') are prepared by treating a compound of formula (IV') with a non-hydroxyl anionic cyclizing agent in an inert solvent. The preferred non-hydroxyl amonic cyclizing agents which can be used in the reaction are the alkali metal alkoxides such as lithium, potassium and especially sodium methoxides, ethoxides, and the like, alkyl lithium such as butyl lithium, octyl lithium and the like and alkali metal hydrides such as lithium, potassium and especially sodium hydride. Although the particular solvent used in the reaction is not critical, monoglyme and diglyme are the preferred solvents when alkali metal alkoxides are used as the cyclizing agent, and hydrocarbons such as hexane or ethers such as tetrahydrofuran are preferred when an alkyl lithium or an alkali metal hydride is used as the cyclizing agent. It is preferred that the reaction be carried out in an inert atmosphere when alkyl lithium or alkali metal hydrides are used as the cyclizing agents. The inert atmosphere is preferably nitrogen, argon, helium and the like, especially nitrogen. The temperature at which the reaction is carried out is not critical, but it is preferred that the reaction be run at about room temperature to 200°C especially at the reflux temperature of the system. Although the time is not critical, the reaction should be run for from 30 minutes to 8 hours for optimum results. The product is recovered by conventional techniques, for example, recrystallization.

The compounds of formulas (Ia) and (Ib) can be prepared by the following reaction from the compounds of formula (Ic):

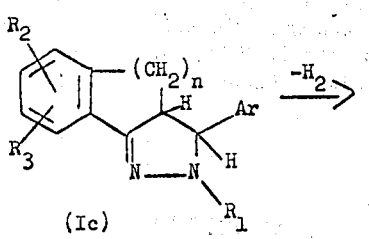

(Ic)

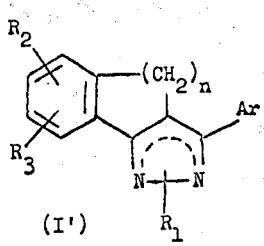

(I')

where $n$, $R_1$, $R_2$, $R_3$ Ar and the proviso are as set out above.

The compounds of formula (I') are prepared by dehydrogenating a compound of formula (Ic). The dehydrogenation can be carried out by exposing compound (Ic) to oxygen, for example, on a chromatographic media such as silica or alumina. Alternately, the reaction may be carried out in the presence of a dehydrogenating agent such as sulfur or palladium or an oxidizing agent such as manganese dioxide or lead dioxide plus acid. Although a solvent is not essential in the reaction and the temperature is not critical, it is preferred that an inert solvent be used and that the reaction be carried out between temperatures of 20° to 250°C. When sulfur or palladium is used as the dehydrogenation agent, the preferred solvents are decalin xylene, naphthalene and the like and the preferred temperature is 200° to 250°C. With manganese dioxide, the preferred solvent is benzene, toluene and the like, and the preferred temperature is 20° to 50°C. When lead dioxide and acetic acid are used in the reaction, the preferred solvent is excess acetic acid and the preferred temperature of the reaction is 20° to 50°C. For optimum results, it is further preferred that the reaction be run for 5 to 50 hours, especially from 5 to 25 hours. The products are recovered by conventional techniques, e.g., evaporation and recrystallization.

The compounds of formula (I''') having the structure (Ia) when $R_1$ is lower alkyl and structures (Ia) and (Ib) when $R_1$ is hydrogen may be prepared in accordance with the following reaction scheme:

where
X is —$COOR_7$ or —CN
$R''_1$ is Li or lower alkyl having 1 to 4 carbon atoms, but excluding tertiary butyl,
$R_6$ is alkyl having 1 to 8 carbon atoms,
$R_7$ is lower alkyl as defined above and
$n$, $R_1$, $R_2$, $R_3$, Ar and the proviso are as set out above, provided $R''_1$ is Li only when $R_1$ is hydrogen.

The compounds of formula (I''') are prepared by treating a compound of the formula (V) with a compound of the formula (VI) and then treating the lithiated intermediate (Va) with a compound of the formula (VII) all under an inert atmosphere and in an inert solvent. The inert atmosphere is preferably nitrogen, argon, helium and the like especially nitrogen. The particular inert solvent used is not critical and can be any of the solvents used in lithiation reactions, preferably, diethyl ether, dioxane and especially tetrahydrofuran. The temperature also is not critical, but it is preferred that the reaction be carried out between —50° to 30°C and especially between about —10° to about 10°C. For optimum results after all reactants are added, the reaction mixture is refluxed for about one hour. In finishing the reaction, when X is —CN, after compound (VII) has reacted, the reaction medium must be made acidic and aqueous to complete the hydrolysis and effect cyclization to compound (I'''). When X is —$COOR_7$, acidification is preferred, but hydrolysis only, by the addition of water, is necessary. The product is isolated by conventional techniques, e.g., evaporation and recrystallization.

The compounds of formulas (Ia) and (Ib) may also be prepared by the following reaction scheme:

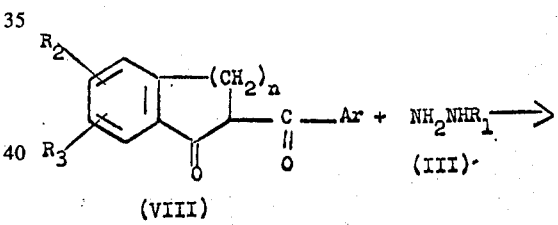

(VIII)

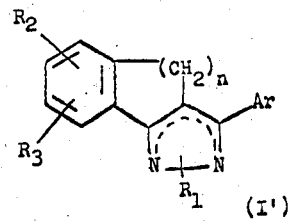

(I')

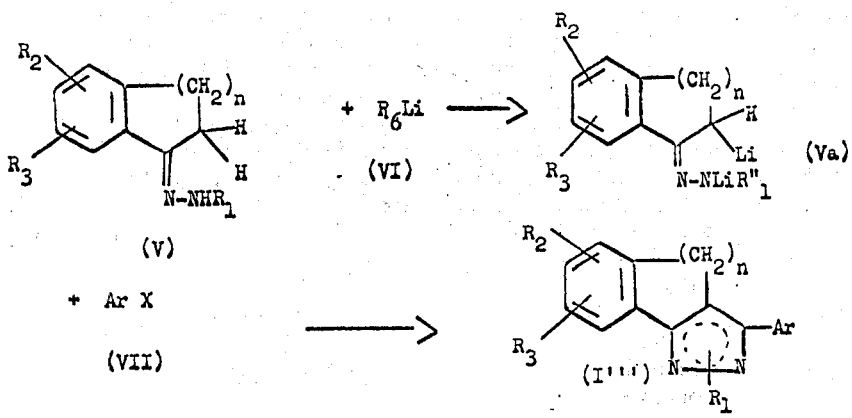

where $n$, $R_1$, $R_2$, $R_3$, Ar and the proviso are as set out above.

The compounds of formula (I') are prepared by treating a compound of the formula (VIII) with a compound of the formula (III). Although a solvent is not necessary, it is preferred that the reaction be carried out in an inert solvent such as the lower alkanols, e.g., methanol, ethanol, and so on, ethers, e.g., diethyl ether, dioxane or tetrahydrofuran, halogenated hydrocarbons such as chloroform, or in excess reactant of formula (III). the temperature of the reaction is not critical, but the reaction is preferably run at between 30° to 150°C, especially at the reflux temperature of the reaction mixture. The product is isolated by standard techniques, e.g., recrystallization.

The compounds of formula (II) are prepared in accordance with the following reaction scheme:

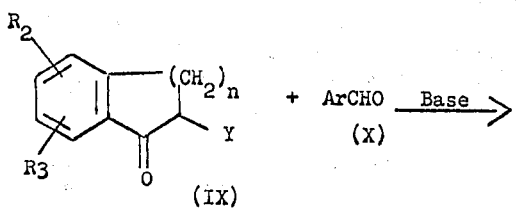

+ ArCHO (X) $\xrightarrow{\text{Base}}$

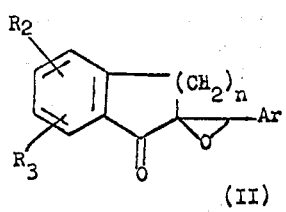

where

Y is a leaving group and $n$, $R_2$, $R_3$, Ar and the proviso are as set out above.

The compounds of formula (II) are prepared by treating the compounds of formula (IX) with the compounds of formula (X) under basic conditions in an inert solvent. It is preferred that the reaction be run in an inert atmosphere such as argon, helium and especially nitrogen. The leaving group Y in formula (IX) can be any of the conventional leaving groups employed in such a reaction, such as chlorine, bromine, iodine, tosylate, mesylate and the like. The preferred leaving group is the halogens, especially chlorine or bromine. The basic conditions for the reaction are provided by alkali or alkali earth metal hydroxides, alkali metal lower alkoxides, tertiary aliphatic and aromatic amines and tertiary cyclic amines such as pyridine and the like. Although the particular solvent used is not critical, the lower alkanols such as methanol, ethanol, butanol and the like are especially preferred, in particular the lower alkanol corresponding to the alkali metal alkoxide when used. The temperature of the reaction is not critical, but it is generally carried out between 0° and 30°C, preferably about 5° to 10°C. Although the time is not critical, it is preferred that the reaction be run for from 1 to 5 hours. The product is recovered by standard techniques, e.g., by crystallization or distillation and is in the form of a mixture of cis and trans isomers one form of which may predominate which can be separated when desired by standard methods, e.g., fractional crystallization.

The compounds of formula (II') can also be prepared by the following reaction scheme:

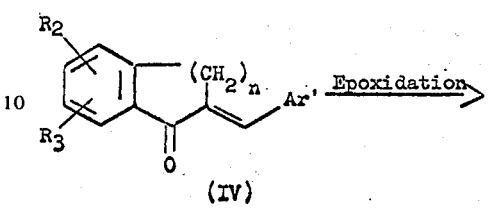

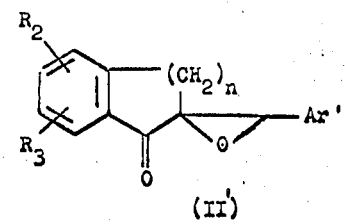

where

Ar' is 4-pyridyl or

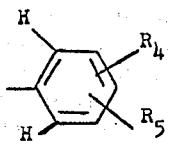

and $n$, $R_2$, $R_3$, $R_4$, $R_5$ and the proviso are as set out above.

The compounds of formula (II') as a mixture of cis and trans isomers are prepared by treating the compounds in cis or trans form or in the form of a mixture of cis and trans isomers of formula (IV'') with an epoxidizing agent in an inert solvent. The epoxidizing agent used can be any of the standard epoxidizing agents used in epoxidizing α, β-unsaturated ketones, e.g., hydrogen peroxide and bases such as the alkali metal hydroxides or alkoxides. The inert solvent can be water, lower alkanols, aliphatic or aromatic hydrocarbons, halogenated hydrocarbons, straight chain ethers, cyclic ethers, and the like depending on the solubility characteristics of the reactants, in particular, the epoxidizing agents. The preferred solvents are water and the lower alkanols such as methanol, ethanol, butanol, and the like. The temperature of the reaction is not critical, but it is normally carried out between 0° and 100°C, depending on the epoxidizing agent but preferably between 15° to 30°C. For It is further preferred that the reaction be run from 3 hours to 3 days preferably 5 to 10 hours. The product is recovered in the usual manner e.g., by extraction and evaporation.

The compounds of formulas (IV) or (IV''), (V), and (IX) are prepared by well known procedures from compounds of the formula:

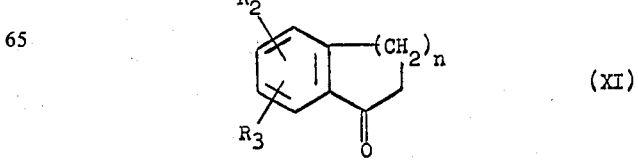

where n, $R_2$, $R_3$ and the proviso are as set out above.

The compounds of formulas (IV) or (IV'') in the form of a mixture of cis and trans isomers are, for example, prepared by treating a compound of formula (XI) with a compound of formula (X). The process is suitably carried out by standard techniques, preferably in an inert solvent such as ethanol or piperidine using a catalytic amount of a base such as sodium hydroxide, potassium hydroxide, diethylamine or triethylamine or in the presence of a catalytic amount of an acid such as hydrochloric acid, sulfuric acid, phosphoric acid, acetic acid, toluenesulfonic acid or methylsulfonic acid. The temperature of the reaction is 15° to 100°, usually 25° to 80°C, and the reaction is run for from 2 to 24 hours, normally 6 to 14 hours. the particular solvent, temperature or time used in the reaction is not critical.

The compounds of formula (V) are prepared by the reaction of compound (XI) with a compound of formula (III) which may be carried out in a conventional manner, for example, by treating the ketone (XI) with the desired hydrazine compound in an inert solvent such as toluene, ethyl alcohol, tetrahydrofuran or dioxane. The temperature of the reaction is normally between 10° to 50°, preferably 20° to 35°, and the time of the reaction is usually 1 to 6 hours. The particular solvent, the temperature and time used in the reaction are not critical.

The compounds of formula (IX) may be obtained by standard procedure from compounds of formula (XI). For example, the chlorine or bromine substituted compounds can be prepared by treating the compound of formula (XI) with chlorine or bromine, preferably in an inert solvent such as acetic acid, chloroform or carbon tetrachloride. The reaction can be carried out at temperatures from room temperature to 50° over a period of 1 to 12 hours, preferably 3 to 6 hours. The particular solvent, temperature or time used in the reaction are not critical.

The tosylate and mesylate can be prepared from the chlorine or bromine substituted compound by treatment with a tosylate or mesylate salt, such as sodium or potassium tosylate or mesylate in an inert solvent such as the above lower alcohols, toluene or benzene. The reaction is preferably carried out at temperatures between 15° to 70° especially between 25° to 40° for a period of 2 to 10 hours, preferably 4 to 7 hours. The particular solvent used, the temperature and the time of the reaction are not critical.

The compounds of formula (IV') can be prepared by the following reaction scheme:

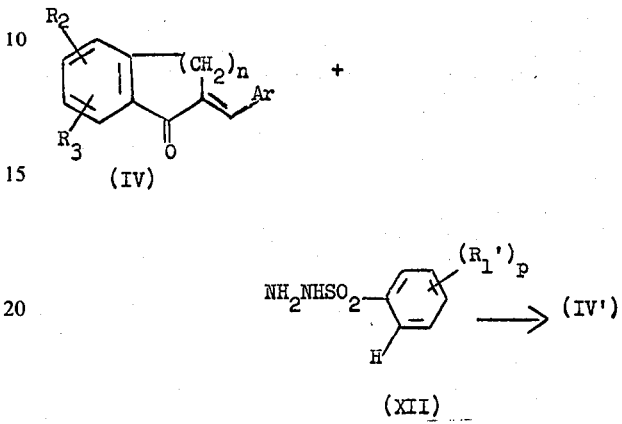

where n, p, $R_1'$, $R_2$, $R_3$, Ar and the proviso are as set out above.

The compounds of formula (IV') are prepared by treating a compound of formula (IV) with a compound of formula (XII) in an inert solvent at a temperature of 15° to 50°C, in the presense of a mineral acid catalyst. The inert solvent is preferably a lower alcohol having 1 to 4 carbon atoms, e.g., methanol, ethanol and the like. The mineral acid can be hydrochloric acid, phosphoric acid or sulfuric acid and it is preferred that the reaction be run for from about 5 hours to 30 hours. The particular solvent, acid, temperature or time employed in the reaction is not critical. The product (IV') is recovered by conventional techniques, e.g., crystallization.

The compounds of formula (VIII) can exist in the following tautomeric forms:

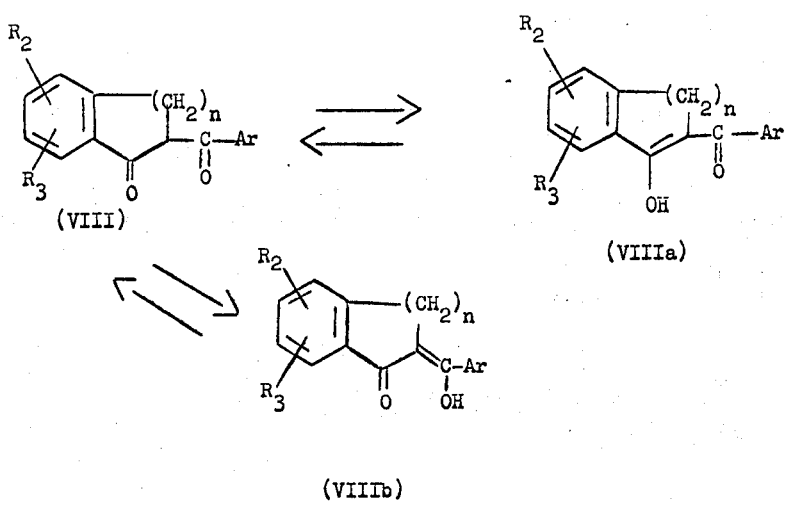

where n, $R_2$, $R_3$, Ar and the proviso are as previously defined. For convenience, structure (VIII) only is used, although all three forms are contemplated.

The compounds of formula (III) and many of the compounds of formula (VI), (VII), (VIII), (X) (XI) and (XII) are known and are prepared by procedures disclosed in the literature. The compounds of formula (VI), (VII), (VIII), (X), (XI), and (XII) not specifically disclosed in the literature may be prepared by analgous methods using known starting materials.

The compounds of formula (I) are useful because they possess pharmacological activity in animals. In particular, the compounds are useful as hypotensive/anti-hypertensive agents, as indicated by their activity in renal hypertensive rats given 10 to 100 mg/kg of active compound using the techniques of A. Grollman (Proc, Soc. Exptl, Biol, and Med. 57:102, 1944) and indirectly measuring the blood pressure from the caudal artery in the tail using a pneumatic pulse transducer.

The compounds of formula (I), including the compound of formula (I) in which n is 1, $R_1$, $R_2$ and $R_3$ are hydrogen and Ar is unsubstituted phenyl, in particular, the compounds of formula (I) having structures (Ia) and (Ib) when $R_1$ is hydrogen or structure (Ib) when $R_1$ is lower alkyl as defined above, especially the compounds in which n is 2, $R_1$ is hydrogen, and Ar is pyridyl or substituted phenyl, e.g., 4,5-dihydro-3-(4-pyridyl)-2H-naphtho[1,2-c]pyrazole, are also useful as anti-fertility agents as indicated by their activity in female Wistar rats which are injected daily with 2 mg of the compound for eight successive days starting on the day of vaginal cornification. At the time of the 4th injection, males of known fertility are cohabitated with the females (one female with one male) until the end of the treatment period. The males are separated from the females 24 hours following the last injection. The females are sacrificed six days later, and examined for the presence of absence of implantation sites.

The use of the compounds as anti-fertility agents is further indicated by their luteolytic properties which results in the compounds being abortifacient agents. The luteolytic activity is determined using pseudopregnant rabbits treated with corn oil or 1 to 100 mg. per day of a compound of formula (I) suspended in corn oil on days 3 through 8 of pseudopregnancy. Blood samples are obtained daily throughout the length of pseudopregnancy. Plasma samples are analyzed for progestin content according to the method of Johansson et al (Endocrinology 82, 143, 1968). The compound is judged active if plasma progestin levels are similar to pretreatment values on day 12 of pseudopregnancy.

Abortifacient activity is also determined in female proestrous rats (Royal Hart, Wistar strain) selected from a colony and caged with fertile males. On the following day pregnancy is confirmed by the presence of spermatozoa in the viginal smear. On the seventh day following mating the females are treated with 1 to 30 milligrams of the compound to be tested. The animals are injected daily for a total of seven days; and on the eighth day following the first injection the animals are killed and the uterus checked for the presence or absence of implantation sites.

The compounds of formula (I), when used as anti-fertility agents exhibit none of the estrogenic effects and side effects exhibited by the steroidal type compounds used for these purposes.

When the compounds are employed for the above utilities, they may be combined with one or more pharmaceutically acceptable carriers or adjuvants, and may be administered orally in such forms as tablets, capsules, elixirs, suspensions and the like, e.g., bucally or sub-liqually as a tablet, parenterally in the form of an injectable solution or suspension or in special forms such as suppositories, e.g., vaginal inserts, pessaries, and the like. Depending upon the compound employed and the mode of administration the exact dosage utilized may vary.

Furthermore, the compounds of formula (I) may be similarly administered in the form of their non-toxic pharmaceutically acceptable acid addition salts. Such salts possess the same order of activity as the free base, are readily prepared by reacting the base with an appropriate acid and accordingly, are included within the scope of the invention. Representative of the acid addition salts are the mineral acid salts, such as the hydrochloride, hydrobromide, sulfate, phosphate and the like and the organic acid salts, such as the malate succinate, benzoate, acetate, methanesulfonate, gluconate, p-toluenesulfonate, benzenesulfonate, naphthalenesulfonate, and the like.

In general, satisfactory results are obtained when these compounds are administered as a hypotensive/anti-hypertensive agent at a daily dosage of about 2 milligrams to about 200 milligrams per kilogram of animal body weight. This daily dosage is preferably administered 2 to 4 times a day, or in sustained release form. For most large mammals, such as primates, the total daily dosage is from about 150 milligrams to about 2000 milligrams. Dosage forms suitable for internal use comprise from about 37.5 milligrams to about 1000 milligrams of the active compound in intimate admixture with a solid or liquid pharmaceutically acceptable carrier or diluent.

When the compounds of formula (I) are administered as an antifertility agent, satisfacory results are obtained at a daily dosage of about 1.0 milligrams to about 200 milligrams orally, subcutaneously or intramuscularly per kilogram of animal body weight. This daily dosage is preferably administered 1 to 4 times a day or in sustained release form. For most large mammals, such as primates, the total daily dosage is from about 1 milligram to about 600 milligrams. Dosage forms suitable for internal use comprise from about 0.25 milligrams to about 300 milligrams of the active compound in intimate admixture with a solid or liquid pharmaceutically acceptable carrier or diluent.

A representative formulation suitable for intramuscular administration once a day in fertility control is an injectable suspension prepared by standard techniques which contain the following:

| Ingredients | Weight (mg) |
| --- | --- |
| 4,5-dihydro-3-(4-pyridyl)-2H-naphtho[1,2-c]pyrazole | 200 |
| sodium carboxy methyl cellulose U.S.P. | 1.25 |
| methyl cellulose | 0.4 |
| polyvinylpyrrolidone | 5 |
| lecithin | 3 |
| benzyl alcohol | 0.01 |
| buffer agent to adjust pH for desired stability | q.s. |
| water | for injection q.s. to 2 |

EXAMPLE 1

4,5-dihydro-3-(4-pyridyl)-2H-naphtho[1,2-c]pyrazole

Step A:
3'-(4-pyridyl)-spiro[1,2,3,4-tetrahydronaphthalene-2,2'-oxirane]-1-one.

To a stirred solution of 11.3 g of 2-bromo-α-tetralone and 5.5 g. of pyridine-4-carboxaldehyde in 20 ml of methanol under nitrogen is added at 5° to 10°C a solution of sodium methoxide in methanol (prepared by dissolving 1.15 g of sodium in 50 ml methanol). After 2 hours, 3'-(4-pyridyl)-spiro[1,2,3,4-tetrahydronaphthalene-2,2'-oxirane]-1-one precipitates and is filtered off and recrystallized from methanol (m.p. 180°–182°C).

When an equivalent amount of
- a. 2-bromo-6-chloro-α-tetralone;
- b. 2-bromo-6-methyl-α-tetralone;
- c. 2-bromo-6,7-dimethoxy-α-tetralone;
- d. 2-bromo-6-trifluoromethyl-α-tetralone or
- e. 2-bromo-6,7-methylenedioxy-α-tetralone; is used in place of the 2-bromo-α-tetralone above there is obtained a. 3'-(4-pyridyl)-spiro[6-chloro-1,2,3,4-tetrahydronaphthalene-2,2'-oxirane]-1-one; (m.p. 155°C);
  b. 3'-(4-pyridyl)-spiro[6-methyl-1,2,3,4-tetrahydronaphthalene-2,2'-oxirane]-1one; (m.p. 147°C);
  c. 3'-(4-pyridyl)-spiro[6,7-dimethoxy-1,2,3,4-tetrahydronaphthalene-2,2'-oxirane]-1-one; (m.p. 197°–200°C);
  d. 3'-(4-pyridyl)-spiro[6-trifluoromethyl-1,2,3,4-tetrahydronaphthalene-2,2'-oxirane]-1-one or
  e. 3'-(4-pyridyl)-spiro[6,7-methylenedioxy-1,2,3,4-tetrahydronaphalene-2,2' oxirane]-1-one (m.p. 166°–168°C) respectively.

When an equivalent amount of
- f. 2-thiophenealdehyde;
- g. 2-furfural;
- h. 2-pyrrolealdehyde;
- i. pyridine-2-carboxaldehyde;
- j. pyridine-3-carboxaldehyde;
- k. p-chlorobenzaldehyde or
- l. p-methoxybenzaldehyde is used in place of the pyridine-4-carboxaldehyde above, there is obtained
- f. 3'-(2-thienyl)-spiro[1,2,3,4-tetrahydronaphthalene-2,2'-oxirane]-1-one;
- g. 3'-(2-furyl)-spiro[1,2,3,4-tetrahydronaphthalene-2,2'-oxirane]-1-one;
- h. 3'-(2-pyrrolyl)-spiro[1,2,3,4-tetrahydronaphthalene-2,2'-oxirane]-1-one;
- i. 3'-(2-pyridyl)-spiro[1,2,3,4-tetrahydronaphthalene-2,2'-oxirane]-1-one;
- j. 3'-(3-pyridyl)-spiro[1,2,3,4-tetrahydronaphthalene-2,2'-oxirane]-1-one;
- k. 3'-(p-chlorophenyl)-spiro[1,2,3,4-tetrahydronaphthalene-2,2'-oxirane]-1-one or
- l. 3'-(p-methoxyphenyl)-spiro[1,2,3,4-tetrahydronaphthalene-2,2'-oxirane]-1-one respectively.

Step B: 4,5-dihydro-3-(4-pyridyl)-2H-naphtho[1,2-c]pyrazole.

A mixture of 3 g. of oxirane from Step A, 15 ml of 98% hydrazine, 5 mg. p-toluenesulfonic acid and 15 ml of n-butyl alcohol are refluxed together for 3 days. On cooling the mixture, 4,5-dihydro-3-(4-pyridyl)-2H-naphtho[1,2-c] pyrazole precipitates and is recovered by filtration (m.p. of base 229°C; m.p. of hydrochloride salt >300°C; m.p. of malate 209-210°C; m.p. of methanesulfonate 273°–276°C; m.p. of 1.5 naphthalenedisulfonate >300°C; m.p. of gluconate 145°–146°C; m.p. of phosphate 273°–276°C).

The 4,5-dihydro-3-(4-pyridyl)-2H-naphtho[1,2-c]pyrazole of this example is an effective fertility control agent when it is subcutaneously administered to an animal at a dosage of 50 milligrams four times a day.

Following the above procedure, but using an equivalent amount of
a. 3'-(4-pyridyl)-spiro[6-chloro-1,2,3,4-tetrahydronaphthalene-2,2'-oxirane]-1-one;
b. 3'-(4-pyridyl)-spiro[6-methyl-1,2,3,4-tetrahydronaphthalene-2,2'-oxirane]-1-one;
c. 3'-(4-pyridyl)-spiro[6,7-dimethoxy-1,2,3,4-tetrahydronaphthalene-2,2'-oxirane]-1-one;
d. 3'-(4-pyridyl)-spiro[6-trifluoromethyl-1,2,3,4-tetrahydronaphthalene-2,2'-oxirane]-1-one;
e. 3'-(4-pyridyl)-spiro[6,7-methylenedioxy-1,2,3,4-tetrahydronaphthalene-2,2'-oxirane]-1-one;
f. 3'-(2-thienyl)spiro[1,2,3,4-tetrahydronaphthalene-2,2'-oxirane]-1-one;
g. 3'-(2-furyl)-spiro[1,2,3,4-tetrahydronaphthalene-2,2'-oxirane]-1-one;
h. 3'-(2-pyrrolyl)-spiro[1,2,3,4-tetrahydronaphthalene-2,2'-oxirane]-1-one;
i. 3'-(2-pyridyl)-spiro[1,2,3,4-tetrahydronaphthalene-2,2'-oxirane]-1-one;
j. 3'-(3-pyridyl)-spiro[1,2,3,4-tetrahydronaphthalene-2,2'-oxirane]-1-one;
k. 3'-(p-chlorophenyl)-spiro[1,2,3,4-tetrahydronaphthalene-2,2'-oxirane]-1-one or
l. 3'-(p-methoxyphenyl)-spiro[1,2,3,4-tetrahydronaphthalene-2,2'-oxirane]-1-one in place of the 3'-(4-pyridyl)-spiro[1,2,3,4-tetrahydronaphthalene-2,2'-oxirane]-1-one used therein, there is obtained
a. 7-chloro-4,5-dihydro-3-(4-pyridyl)-2H-naphtho[1,2-c]pyrazole; (m.p. 250°–252°C);
b. 7-methyl-4,5-dihydro-3-(4-pyridyl)-2H-naphtho[1,2-c]pyrazole; (mp 222°–224°C);
c. 7,8-dimethoxy-4,5-dihydro-3-(4-pyridyl)-2H-naphtho[1,2-c]pyrazole; (m.p. 245°C);
d. 7-trifluoromethyl-4,5-dihydro-3-(4-pyridyl)-2H-naphtho[1,2-c]pyrazole;
e. 7,8-methylenedioxy-4,5-dihydro-3-(4-pyridyl)-2H-naphtho[1,2-c]pyrazole; (m.p. 198°–200°C).
f. 4,5-dihydro-3-(2-thienyl)-2H-naphtho[1,2-c]pyrazole; (mp 211-213°C);
g. 4,5-dihydro-3-(2-furyl)-2H-naphtho[1-2-c]pyrazole; (mp 160-161°C);
h. 4,5-dihydro-3-(2-pyrrolyl)-2H-naphtho[1,2-c]pyrazole; (mp 229-230°C);
i. 4,5-dihydro-3-(2-pyridyl)-2H-naphtho[1,2-c]pyrazole(m.p. 182-184°C);
j. 4,5-dihydro-3-(3-pyridyl)-2H-naphtho[1,2-c]pyrazole(m.p. 226-228°C);
k. 4,5-dihydro-3-(p-chlorophenyl)-2H-naphtho[1,2-c]pyrazole (m.p. 194-195°C) or
l. 4,5-dihydro-3-(-p-methoxyphenyl)-2H-naphtho[1,2-c]pyrazole(m.p. 161-163°C) respectively When an equivalent amount of 2-bromo-benzo[b]cycloheptanone is substituted for the 2-bromo-α-tetralone in step A above, there is obtained following the processes of steps A and B, 3-(4-pyridyl)-2,4,5,6-tetrahydrobenzo[6,7]cyclohepta[1,2-c]pyrazole, (mp 217-219°C).

EXAMPLE 2

3-(p-chlorophenyl)-2-Methyl-4H-indeno[1,2-c]pyrazole

Step A: 3'-(p-chlorophenyl)-spiro[indan-2,2'-oxirane]-1-one

To a stirred solution of 2-bromo indanone and 5 g. of p-chloro-benzaldehyde in 20 ml of methanol under nitrogen is added at 5° to 10°C a solution of sodium methoxide in methanol (prepared by dissolving 1.15 g. of sodium in 50 ml of methanol). After 2 hours, 3'-(p-chlorophenyl)-spiro[indan-2,2'-oxirane]-1-one precipitates and is filtered off and recrystallized from methanol.

Following essentially the same procedure as above but using an equivalent amount of
- a. 4-methylbenzaldehyde;
- b. 3,4-dichlorobenzaldehyde;
- c. 3,4-dimethoxybenzaldehyde;
- d. 3-trifluoromethylbenzaldehyde;
- e. 3,4-methylenedioxybenzaldehyde;
- f. 2-thiophenealdehyde;
- g. 2-furfural;
- h. 2-pyrrolealdehyde;
- i. pyridine-4-carboxaldehyde;
- j. pyridine-3-carboxaldehyde or
- k. pyridine-2-carboxaldehyde in place of the p-chlorobenzaldehyde, there is obtained
- a. 3'-(p-tolyl)-spiro[indan-2,2'-oxirane]-1-one;
- b. 3'-(3,4-dichlorophenyl)-spiro[indan-2,2'-oxirane]-1-one;
- c. 3'-(3,4-dimethoxyphenyl)-spiro[indan-2,2'-oxirane]-1-one;
- d. 3'-(3-trifluoromethylphenyl)-spiro[indan-2,2'-oxirane]-1-one;
- e. 3'-(3,4-methylenedioxyphenyl)-spiro[indan-2,2'-oxirane]-1-one;
- f. 3'-(2-thienyl)-spiro[indan-2,2'-oxirane]-1-one;
- g. 3'-(2-furyl)-spiro[indan-2,2'-oxirane]-1-one;
- h. 3'-(2-pyrrolyl)-spiro[indan-2,2'-oxirane]-1-one;
- i. 3'-(4-pyridyl)-spiro[indan-2,2'-oxirane]-1-one;
- j. 3'-(3-pyridyl)-spiro[indan-2,2'-oxirane]-1-one or
- k. 3'-(2-pyridyl)-spiro[indan-2,2'-oxirane]-1-one respectively.

Step B: 3-(p-chlorophenyl)-2-methyl-4H-indeno[1,2-c]pyrazole.

To a solution of 14 g. of 3'-(p-chlorophenyl)-spiro[indan-2,2'-oxirane]-1-one and 2.7 g. of methylthydrazine in 700 ml of absolute ethanol is added 0.9 ml of boron trifluoride etherate, and the mixture is refluxed under nitrogen for 48 hours. The mixture is evaporated to dryness, and the residue is dissolved in chloroform and washed with water. The solution is dried over sodium sulfate and evaporated to dryness. The residue is crystallized from heptane yielding 3-(p-chlorophenyl)-2-methyl-4H-indeno[1,2-c]pyrazole (m.p. 131°-133°C).

Evaporation of the mother liquor from the crystallization yields 3-(p-chlorophenyl)-1-methyl-4H-indeno[1,2-c]pyrazole (m.p. 176°C).

When the above process is carried out using an equivalent amount of hydrazine in place of the methylhydrazine, there is obtained 3-(p-chlorophenyl)-4H-indeno[1,2-c]pyrazole (m.p. 266°-268°C).

Following essentially the same process as above and using an equivalent amount of hydrazine in place of the methylhydrazine and an equivalent amount of
- a. 3'-(p-tolyl)-spiro[indan-2,2'-oxirane]-1-one;
- b. 3'-(3,4-dichlorophenyl)-spiro[indan-2,2'-oxirane]-1-one
- c. 3'-(3,4-dimethoxyphenyl)-spiro[indan-2,2'-oxirane]-1-one;
- d. 3'-(3-trifluoromethylphenyl)-spiro[indan-2,2'-oxirane]-1one;
- e. 3'-(3,4-methylenedioxyphenyl)-spiro[indan-2,2'-oxirane]-1-one;
- f. 3'-(2-thienyl)-spiro[indan-2,2'-oxirane]-1-one;
- g. 3'-(2-furyl)-spiro[indan-2,2'-oxirane]-1-one;
- h. 3'-(2-pyrrolyl)-spiro[indan-2,2'-oxirane]-1-one;
- i. 3'-(4-pyridyl)-spiro[indan-2,2'-oxirane]-1-one;
- j. 3'-(3-pyridyl)-spiro[indan-2,2'-oxirane]-1-one or
- k. 3'-(2-pyridyl)-spiro[indan-2,2'-oxirane]-1-one in place of the 3'-(p-chlorophenyl)-spiro[indan-2,2'-oxirane]-1-one, there is obtained
- a. 3-(p-tolyl)-4H-indeno[1,2-c]pyrazole (250°-252°C);
- b. 3-(3,4-dichlorophenyl)-4H-indeno[1,2-c]pyrazole (m.p. 252°C);
- c. 3-(3,4-dimethoxyphenyl)-4H-indeno[1,2-c]pyrazole (m.p. 231°C);
- d. 3-(3-trifluoromethylphenyl)-4H-indeno[1,2-c]pyrazole (260°-262°C);
- e. 3-(3,4-methylenedioxyphenyl)-4H-indeno[1,2-c]pyrazole (285°-287°C);
- f. 3-(2-thienyl)-4H-indeno[1,2-c]pyrazole (220°-221°C)
- g. 3-(2-furyl)-4H-indeno[1,2-c]pyrazole (186°-188°C);
- h. 3-(2-pyrrolyl)-4H-indeno[1,2-c]pyrazole (m.p. 215°-218°C.);
- i. 3-(4-pyridyl)-4H-indeno[1,2-c]pyrazole (m.p. 270°-272°C);
- j. 3-(3-pyridyl)-4H-indeno[1,2-c]pyrazole (m.p. 229°-231°C) or
- k. 3-(2-pyridyl)-4H-indeno[1,2-c]pyrazole (m.p. 216°-218°C) respectively.

EXAMPLE 3

3-(p-chlorophenyl)-1-methyl-4H-indeno[1,2-c]pyrazole

To a mixture of 25 g of 2-(p-chlorobenzylidine)-1-indanone and 5 g. of methylhydrazine in 150 ml of ethanol is added sufficient chloroform to dissolve all the reactants. The solution is refluxed overnight under anhydrous conditions. After cooling, the reaction mixture is filtered and the solvent removed by evaporation. The residue is chromatographed on silica using benzene as the eluant to yield 3-(p-chlorophenyl)-1-methyl-4H-indeno[1,2-c]pyrazole (m.p. 176°C); 3-(p-chlorophenyl)-2-methyl-4H-indeno[1,2-c]pyrazole (m.p. 131°-133°C) and 2,3,3a,4-tetrahydro-3-(p-chlorophenyl)-2-methyl-indeno[1,2-c]pyrazole (m.p. 122°C).

When the above process is carried out using equivalent amounts of 2-(4'-pyridylmethylene)-3,4-dihydro-1(2H)-naphthalenone and hydrazine in place of the 2-(p-chlorobenzylidene)-1-indanone and methyl hydrazine, there is obtained 4,5-dihydro-3-(4-pyridyl)-2H-naphtho[1,2-c]pyrazole (m.p. 229°C), and 3-(4-pyridyl)-3,3a,4,5-tetrahydro-2H-naphtho[1,2-c]pyrazole (m.p. 169°-173°C).

EXAMPLE 4

4,5-dihydro-3-(4-pyridyl)-2H-naphtho[1,2-c]pyrazole

To a mixture of 10 g. of 2-(4-pyridylmethylene)-3,4-dihydro-1(2H)-naphthalenone in 100 ml of water and 200 ml of ethanol is added sufficient chloroform to dissolve the reactants. The pH is adjusted to between 7 and 9 and a 3 molar excess of 30% hydrogen peroxide in water is added dropwise at room temperature. The reactants are stirred for 5 hours after which sufficient ferrous sulfate is added to neutralize the excess peroxide. The mixture is then acidified with hydrochloric acid and the organic solvent evaporated off. The water solution remaining is made basic and extracted with chloroform. The chloroform is evaporated off yielding 3'-(4-pyridyl)-spiro[1,2,3,4-tetrahydronaphthalene-2,2'-oxirane]-1-one.

Following the procedure of step B of Example 1, the above 3'-(4-pyridyl)-spiro[1,2,3,4-tetrahydronaphthalene-2,2'-oxirane]-1-one is treated with hydrazine to yield 4,5-dihydro-3-(4-pyridyl)-2H-naphtho[1,2-c]pyrazole.

EXAMPLE 5

4,5-dihydro-3-(4-pyridyl)-2H-naphtho[1,2-c]pyrazole

To a solution of 4 grams of 1,2,3,4-tetrahydro-α-naphthyl hydrazone in 100 milliliters of tetrahydrofuran at 0°C is added under nitrogen with stirring 5 grams of n-butyl lithium in hexane. After the n-butyl lithium has reacted, 2 grams of isonicotinic acid methyl ester in 25 milliliters of tetrahydrofuran is added. The mixture is stirred at 0° for 15 minutes, and then heated with 100 milliliters of 3N-hydrochloric acid under reflux for 1 hour and cooled. The aqueous layer is made basic with sodium bicarbonate and extracted 3 times with 50 milliliters of ether. The combined organic layers are concentrated, and the 4,5-dihydro-3-(4-pyridyl)-2H-naphtho[1,2-c]pyrazole (m.p. 229°C) is recrystallized from 95% ethanol.

When the above process is repeated using an equivalent amount of isonicotinyl nitrile in place of the isonicotinic acid methyl ester, there is again obtained 4,5-dihydro-3-(4-pyridyl)-2H-naphtho[1,2-c]pyrazole.

EXAMPLE 6

4,5-dihydro-3-(4-pyridyl)-2H-naphtho[1,2-c]pyrazole

A solution of 12.5 grams of 2-isonicotinoyl-α-tetralone and 2 grams of hydrazine in 50 milliliters of ethanol is refluxed for 1 hour. The solution is then acidified with 100 milliliters of 1N hydrochloric acid and extracted twice with 100 milliliters of methylene chloride. The aqueous solution is then made basic with sodium bicarbonate and extracted again with methylene chloride. The latter extracts are washed with water, dried and concentrated under vacuum. The 4,5-dihydro-3-(4-pyridyl)-2H-naphtho[1,2-c]pyrazole which precipitates is recrystallized from ethanol (m.p. 229°C).

EXAMPLE 7

When an equivalent amount of
a. 2-bromo-5-chloro-indanone;
b. 2-bromo-5-methyl-indanone;
c. 2-bromo-5,6-dimethoxy-indanone;
d. 2-bromo-5-trifluoromethyl indanone or
e. 2-bromo-5,6-methylenedioxy-indanone is used in place of the 2-bromo indanone in Step A of example 2 there is obtained
a. 3'-(p-chlorophenyl)-spiro[5-chloroindan-2,2'-oxirane]-1-one; (m.p. 152°–153°C);
b. 3'-(p-chlorophenyl)-spiro[5-methylindan-2,2'-oxirane]-1-one;
c. 3'-(p-chlorophenyl)spiro[5,6-dimethoxyindan-2,2'-oxirane]-1-one;
d. 3'-(p-chlorophenyl)-spiro[5-trifluoromethylindan-2,2'-oxirane]-1-one or
e. 3'-(p-chlorophenyl)-spiro[5,6-methylenedioxyindan-2,2'-oxirane]-1-one respectively Following the procedure of Step B of Example 2 but using an equivalent amount of hydrazine in place of the methylhydrazine and
a. 3-(p-chlorophenyl)-spiro[5-chloroindan-2,2'-oxirane]-1-one,
b. 3-(p-chlorophenyl)-spiro[5-methylindan-2,2'-oxirane]-1-one,
c. 3-(p-chlorophenyl)-spiro[5,6-dimethoxyindan-2,2'-oxirane]-1-one,
d. 3-(p-chlorophenyl)-spiro [5-trifluoromethylindan-2,2'-oxirane]-1-one, or
e. 3-(p-chlorophenyl)-spiro[5,6-methylenedioxyindan-2,2'-oxirane]-1-one in place of the 3'-(p-chlorophenyl)-spiro[indan-2,2'-oxirane]-1-one used therein, there is obtained
a. 6-chloro-3-(p-chlorophenyl)-4H-indeno[1,2-c]pyrazole (m.p. 280°C);
b. 6-methyl-3-(p-chlorophenyl)-4H-indeno[1,2-c]pyrazole (m.p. 294°–295°C);
c. 6,7-dimethoxy-3-(p-chlorophenyl)-4H-indeno[1,2-c]pyrazole (m.p. 235°C);
d. 6-trifluoromethyl-3-(p-chlorophenyl)-4H-indeno[1,2-c]pyrazole or
e. 6,7-methylenedioxy-3-(p-chlorophenyl)-4H-indeno[1,2-c]pyrazole (m.p. 278°C) respectively.

EXAMPLE 8

3-(p-totyl)-4H-indeno[1,2-c]pyrazole

Step A: 2-p-Toluoylindan-1-one.

To a suspension of 7.8 g. of sodium amide in 100 ml. anhydrous ether under an atmosphere of nitrogen is added 13.2 g. of indan-1-one. Ammonia is evolved and the mixture is stirred and heated under reflux until evolution ceases, after about 1 hour. A solution of 21.2 g. of phenyl p-toluate in 250 ml. of ether is then added dropwise over a period of 15 min. and the resulting mixture is heated under reflux for 1½ hr. It is then cooled and poured onto 500 g. of ice, and then made slightly acidic by the addition of 2N hydrochloric acid. The organic layer is separated and washed twice with a 10% solution of sodium bicarbonate and once with water. It is then shaken with a saturated aqueous solution of cupric acetate, and the 2-phase system is stirred vigorously overnight. The resulting brown solid produced is filtered off and added to a stirred mixture of 250 ml. of ether and 100 ml of 2N hydrochloric acid. After 1 hr. the ether layer is separated, washed with sodium bicarbonate solution and water and dried over sodium sulfate. Removal of the ether gives a crude crystalline residue which can be recrystallized from ether to give the title product (m.p. 103°–105°).

When the above procedure is carried out using an equivalent amount of
a. 2-thiophene carboxylic acid, phenyl ester;

b. 2-furane carboxylic acid, phenyl ester;
c. 2-pyrrole carboxylic acid, phenyl ester, or
d. m-trifluoromethyl benzoic acid, phenyl ester in place of the phenyl-p-toluate there is obtained
   a. 2-(2-thenoyl)-indan-1-one (m.p. 139°–141°C);
   b. 2-(2-furoyl)-indan-1-one (m.p. 107°–109°C);
   c. 2-(2-pyrroyl)-indan-1-one (m.p. 148°–150°C) or
   d. 2-(m-trifluoromethylbenzoyl)-indan-1-one (m.p. 126°–128°C) respectively.

Following the above procedure but using an equivalent amount of
   e. 2-thiophene carboxylic acid phenyl ester and α-tetralone;
   f. 2-furane carboxylic acid phenyl ester and α-tetralone, or
   g. 2-pyrrole carboxylic acid phenyl ester and α-tetralone in place of the phenyl-p-toluate and indan-1-one, there is obtained
   e. 2-(2-thenoyl)-α-tetralone (m.p. 100°–102°C);
   f. 2-(2-furoyl)-α-tetralone (m.p. 75°–77°C); or
   g. 2-(2-pyrroyl)-α-tetralone (m.p. 137°–140°C), respectively.

Step B: 3-(p-tolyl)-4H-indeno[1,2-c]-pyrazole

To a warm solution of 3.3 g. of the diketone of Step A in 33 ml. of ethanol and 10 ml. of chloroform is added 4 g. of hydrazine and the resulting solution is refluxed for 1 hr. It is then cooled and evaporated to dryness under reduced pressure. The crude solid residue obtained is crystallized from methanol to yield the product 3-(p-tolyl)-4H-indeno[1,2-c]-pyrazole (m.p. 250°–252°C).

When the above procedures are repeated and equivalent amounts of α-tetralone and phenyl isonicotinate are used in place of the indan-1-one and phenyl-p-toluate respectively, there is obtained 4,5-dihydro-3-(4-pyridyl)-2H-naphtho[1,2-c]pyrazole (m.p. 229°C).

Following the above procedure but using an equivalent amount of
   a. 2-(2-thenoyl)-indan-1-one;
   b. 2-(2-furoyl)-indan-1-one;
   c. 2-(2-pyrroyl)-indan-1-one;
   d. 2-(m-trifluoromethylbenzoyl)-indan-1-one;
   e. 2-(2-thenoyl)-α-tetralone;
   f. 2-(2-furoyl)-α-tetralone or
   g. 2-(2-pyrroyl)-α-tetralone in place of the 2-p-toluoylindan-1-one, there is obtained
   a. 3-(2-thienyl)-4H-indeno[1,2-c]pyrazole (m.p. 220°–221°C);
   b. 3-(2-furyl)-4H-indeno[1,2-c]pyrazole (m.p. 186°–188°C);
   c. 3-(2-pyrrolyl)-4H-indeno[1,2-c]pyrazole (m.p. 215°–218°C.);
   d. 3-(m-trifluoromethylphenyl)-4H-indano[1,2-c]pyrazole (m.p. 260°–262°C);
   e. 4,5-dihydro-3-(2-thienyl)-2H-naphtho[1,2-c]pyrazole (m.p. 211°–213°C);
   f. 4,5-dihydro-3-(2-furyl)-2H-naphtho[1,2-c]pyrazole (m.p. 160°–161°C) or
   g. 4,5-dihydro-3-(2-pyrrolyl)-2H-naphtho[1,2-c]pyrazole (m.p. 229°–230°C), respectively.

EXAMPLE 9

3-(4-pyridyl)-2,4,5,6-tetrahydrobenzo[6,7]cyclohepta[1,2-c]pyrazole.

Step A: 2-(4-pyridylmethylene)-2,3,4,5-tetrahydrobenzocycloheptan-1-one

A mixture of 80.0 grams (0.50 Moles) of benzosuberone, 64.2 grams (0.60 moles) of 4-pyridinecarboxaldehyde, 10 grams of piperidine and 10 grams of acetic acid are heated at 80° for 19 hours. The resultant solid is crystallized from about 400 ml. of ethanol to give 2-(4-pyridylmethylene)-2,3,4,5-tetrahydrobenzocycloheptan-1-one (m.p. 108°–109°C).

Following the above procedure but using an equivalent amount of α-tetralone or 8-methoxybenzosuberone in place of the benzosuberone, there is obtained 2-(4-pyridylmethylene)-α-tetralone. (m.p. 112°–114°C) or 8-methoxy-2-(4-pyridylmethylene)-2,3,4,5-tetrahydrobenzocycloheptan-1-one respectively.

Step B: 3-(4-pyridyl)-2,3,3a,4,5,6-hexahydrobenzo[6,7]cyclohepta[1,2-c]pyrazole

To 24.0 grams (0.1 moles) of the above 2-(4-pyridylmethylene)-2,3,4,5-tetrahydrobenzocycloheptan-1-one in a flask equipped with stirrer and condenser are added 4.8 grams (0.15 mole) of hydrazine hydrate (95%) and 150 ml. of isopropanol. The mixture is stirred and refluxed for about 24 hours and the solvent is then removed in vacuo on a rotary evaporator. The solid residue is then crystallized from methanol to give 3-(4-pyridyl)-2,3,3a,4,5,6-hexahydrobenzo[6,7]cyclohepta[1,2-c]pyrazole, (m.p. 152-157°C).

When the above process is carried out using an equivalent amount of 8-methoxy-2-(4-pyridinemethylene)-2,3,4,5-tetrahydrobenzocycloheptan-1-one in place of the 2-(4-pyridine-methylene)-2,3,4,5-tetrahydrobenzocycloheptan-1-one there is obtained 9-methoxy-3-(4-pyridyl)-2,3,3a,4,5,6-hexahydrobenzo[6,7]cyclohepta[1,2-c]pyrazole (m.p. 162°–166°C).

Following the above procedure, but using an equivalent amount of 2-(4-pyridylmethylene)-α-tetralone and methylhydrazine in place of the 2-(4-pyridylmethylene)-2,3,4,5-tetrahydrobenzocycloheptan-1-one and hydrazine hydrate respectively there is obtained 2-methyl-3-(4-pyridyl)-3,3a,4,5-tetrahydro-2H-naphtho[1,2-c]pyrazole (m.p. 195°–198°C).

Step C: 3-(4-pyridyl)-2,4,5,6-tetrahydrobenzo[6,7-]cyclohepta[1,2-c]pyrazole

Into a flask eqipped with a magnetic stirring bar is charged 5.0 grams of 3-(4-pyridyl)-2,3,3a,4,5,6-hexahydrobenzo[6,7]cyclohepta[1,2-c]pyrazole, 25 grams of activated manganese dioxide and 150 ml of dry benzene. The mixture is stirred for about 12 hours at room temperature, after which the manganese salts are filtered off and the solvent removed in vacuo. The solid is crystallized from ethanol to give 3-(4-pyridyl)-2,4,5,6-tetrahydrobenzo[6,7]cyclohepta[1,2-c]pyrazole (m.p. 217°–219°C).

Following the above procedure but using an equivalent amount of 9-methoxy-3-(4-pyridyl)-2,3,3a,4,5,6-hexahydrobenzo[6,7]cyclohepta[1,2-c]pyrazole or 2-methyl-3-(4-pyridyl)-3,3a,4,5-tetrahydro-2H-naphtho[1,2-c]pyrazole in place of the 3-(4-pyridyl)-2,3,3a,4,5,6-hexahydrobenzo[6,7]cyclohepta[1,2-c]pyrazole used therein, there is obtained 9-methoxy-3-(4-pyridyl)-2,4,5,6-tetrahydrobenzo[6,7]cyclohepta[1,2-c]pyrazole (m.p. 200°–201°C) or 2-methyl-3-(4-pyridyl)-4,5-dihydro-2H-naphtho[1,2-c]pyrazole (m.p. 124°–217°C).

EXAMPLE 10

4,5-dihydro-3-(4-pyridyl)-2H-naphtho[1,2-c]pyrazole

Step A: 2-(4-pyridylmethylene)

A mixture of 73.0 grams (0.50 moles) of α-tetralone, 64.2 grams (0.60 moles) of 4-pyridinecarboxaldehyde, 10 grams of piperidine and 10 grams of acetic acid are heated at 80° for 19 hours. The resultant solid is crystallized from about 400 ml. of ethanol to give 2-(4'-pyridylmethylene)-1-tetralone; (m.p. 112°–114°C).

Step b: p-tosylhydrazone of 2-(4'-pyridylmethylene)-1-tetralone.

A mixture of 2.0 grams of 2-(4'-pyridylmethylene)-1-tetralone, 1.89 grams of p-toluenesulfonylhydrazide, 30 ml. of methanol and 0.22 ml. of concentrated hydrochloric acid is stirred at room temperature for about 20 hours. The resultant solid is filtered off, washed with methanol/ether and recrystallized from methanol to give the p-tosylhydrazone of 2-(4'-pyridylmethylene)-1-tetralone; (m.p. 151° dec.)

Step c: 4,5-dihydro-3-(4-pyridyl)-2H-naphtho[1,2-c]pyrazole

To a stirred solution of 2.7 g. (0.05 mole) of sodium methoxide in 50 ml. of diglyme heated to 170° is added 10.1 g (0.025 mole) of the p-tosylhydrazone of 2-(4'-pyridylmethylene)-1-tetralone. The solution refluxed for one hour, concentrated in vacuo and treated with 2.5 ml. of water. The resultant solid is separated and recrystallized from methanol to give 4,5-dihydro-3-(4-pyridyl)2H-naphtho[1,2-c]pyrazole, (m.p. 229°C).

EXAMPLE 11

4,5-dihydro-3-(4-pyridyl)-2H-naphtho[1,2-c]pyrazole

To a stirred mixture of 1.2 g. (0.05 moles) sodium hydride and 50 ml. of anhydrous hexane under a nitrogen atmosphere is added 10.1 g. (0.025 mole) of the p-tosylhydrazone of 2-(4'-pyridylmethylene)-1-tetralone. The resultant mixture is stirred and refluxed for 4 hours. The reaction mixture is cooled in an ice bath and treated with 5 ml of water dropwise. The organic layer is separated, dried with magnesium sulfate, filtered and concentrated to give 4,5-dihydro-3-(4-pyridyl)-2H-naphtho[1,2-c]pyrazole.

EXAMPLE 12

4,5-dihydro-3-(4-pyridyl)-2H-naphtho[1,2-c]pyrazole

Step A: 3'-(4-pyridyl)-spiro[7-methoxy-1,2,3,4-tetrahydronaphthalene-2,2'-oxirane]-1-one When an equivalent amount of 2-bromo-7-methoxy-α-tetralone is used in place of the 2-bromo-α-tetralone in Step A of example 1, there is obtained 3'-(4-pyridyl)-spiro[7-methoxy-1,2,3,4-tetrahydronaphthalene-2,2'-oxirane]-1-one.

When an equivalent amount of
a. benzaldehyde
b. p-tolualdehyde
c. m-tolualdehyde or
d. o-tolualdehyde is used in place of the pyridine-4-carboxaldehyde in Step A of example 1, there is obtained
a. 3'-phenyl-spiro[1,2,3,4-tetrahydronaphthalene-2,2'-oxirane]-1-one;
b. 3'-(p-tolyl)-spiro[1,2,3,4-tetrahydronaphthalene-2,2'-oxirane]-1-one;
c. 3'-(m-tolyl)-spiro[1,2,3,4-tetrahydronaphthalene-2,2'-oxirane]-1-one, or
d. 3'-(o-tolyl)-spiro[1,2,3,4-tetrahydronaphthalene-2,2'-oxirane]1'-one respectively.

Step B: 4,5-dihydro-3-(4-pyridyl)-2H-naphtho[1,2-c]pyrazole.

Three grams of 3'-(4-pyridyl)-spiro[1,2,3,4-tetrahydronaphthalene-2,2'-oxirane]-1-one in 10 ml. of ethyl alcohol is added to 18 ml of 98% hydrazine, 3.5 ml of acetic acid and 12 ml. of dioxane and refluxed for 12 hours. On cooling the mixture, 4,5-dihydro-3-(4-pyridyl)-2H-naphtho[1,2-c]pyrazole precipitates and is recovered by filtration (m.p. of base 229°C; m.p. of hydrochloride salt >300°C).

Following the above procedure, but using from Step A of example 1 or Step A above an equivalent amount of
a. 3'-(4-pyridyl)-spiro[6-chloro-1,2,3,4-tetrahydronaphthalene-2,2'-oxirane]-1-one;
b. 3'-(4-pyridyl)-spiro[6-methyl-1,2,3,4-tetrahydronaphthalene-2,2'-oxirane]-1-one;
c. 3'-(4-pyridyl)-spiro[6,7-dimethoxy-1,2,3,4-tetrahydronaphthalene-2,2'-oxirane]-1-one;
d. 3'-(4-pyridyl)-spiro[6-trifluoromethyl-1,2,3,4-tetrahydronaphthalene-2,2'-oxirane]-1-one;
e. 3'-(4-pyridyl)-spiro[6,7-methylenedioxy-1,2,3,4-tetrahydronaphthalene-2,2'-oxirane]-1-one;
f. 3'-(4-pyridyl)-spiro[7-methoxy-1,2,3,4-tetrahydronaphthalene-2,2'-oxirane]-1-one;
g. 3'-(2-thienyl)-spiro[1,2,3,4-tetrahydronaphthalene-2,2'-oxirane]-1-one;
h. 3'-(2-furyl)-spiro[1,2,3,4-tetrahydronaphthalene-2,2'-oxirane]-1-one;
i. 3'-(2-pyrrolyl)-spiro[1,2,3,4-tetrahydronaphthalene-2,2'-oxirane]-1-one;
j. 3'-(2-pyridyl)-spiro[1,2,3,4-tetrahydronaphthalene-2,2'-oxirane]-1-one;
k. 3'-(3-pyridyl)-spiro[1,2,3,4-tetrahydronaphthalene-2,2'-oxirane]-1-one;
l. 3'-(p-chlorophenyl)-spiro[1,2,3-4-tetrahydronaphthalene-2,2'-oxirane]-1-one;
m. 3'-(p-methoxyphenyl)spiro[1,2,3,4-tetrahydronaphthalene-2,2'-oxirane]-1-one;
n. 3'-phenyl-spiro[1,2,3,4-tetrahydronaphthalene-2,2'-oxirane]-1-one;
o. 3'-(p-tolyl)-spiro[1,2,3-4-tetrahydronaphthalene-2,2'-oxirane]-1-one;
p. 3'-(m-tolyl)-spiro[1,2,3,4-tetrahydronaphthalene-2,2'-oxirane]-1-one,
q. 3'-(o-tolyl)-spiro[1,2,3,4-tetrahydronaphthalene-2,2'-oxirane]-1-one in place of the 3'-(4-pyridyl)-spiro[1,2,3,4-tetrahydronaphthalene-2,2'-oxirane]-1-one used therein, there is obtained
a. 7-chloro-4,5-dihydro-3-(4-pyridyl)-2H-naphtho[1,2-c]pyrazole (m.p. 250°–252°C);
b. 7-methyl-4,5-dihydro-3-(4-pyridyl)-2H-naphtho[1,2-c]pyrazole (m.p. 222°–224°C);
c. 7,8-dimethoxy-4,5-dihydro-3-(4-pyridyl)-2H-naphtho[1,2-c]pyrazole (m.p. 245°C)
d. 7-trifluoromethyl-4,5-dihydro-3-(4-pyridyl)-2H-naphtho[1,2-c]pyrazole;
e. 7,8-methylenedioxy-4,5-dihydro-3-(4-pyridyl)-2H-naptho[1,2-c]pyrazole (m.p. 198°–200°C);
f. 7-methoxy-4,5-dihydro-3-(4-pyridyl)-2H-naphtho[1,2-c]pyrazole (m.p. 168°–170°C)
g. 4,5-dihydro-3-(2-thienyl)-2H-naphtho[1,2-c]pyrazole (m.p. 211°–213°C);
h. 4,5-dihydro-3-(2-furyl)-2H-naphtho[1,2-c]pyrazole (m.p. 160°–161°C);
i. 4,5-dihydro-3-(2-pyrrolyl)-2H-naphtho[1,2-c]pyrazole (m.p. 229°–230°C);
j. 4,5-dihydro-3-(2-pyridyl)-2H-naphtho[1,2-c]pyrazole (m.p. 182°–184°C);

k. 4,5-dihydro-3-(3-pyridyl)-2H-naphtho[1,2-c]pyrazole (m.p. 226°–228°C);
l. 4,5-dihydro-3-(p-chlorophenyl)-2H-naphtho[1,2-c]pyrazole (m.p. 194°–195°C);
m. 4,5-dihydro-3-(p-methoxyphenyl)-2H-naphtho[1,2-c]pyrazole (m.p. 161°–163°C)
n. 4,5-dihydro-3-phenyl-2H-naphtho[1,2-c]pyrazole (m.p. 172°–174°C);
o. 4,5-dihydro-3-(p-tolyl)-2H-naphtho[1,2-c]pyrazole (m.p. 184°–186°C);
p. 4,5-dihydro-3-(m-tolyl)-2H-naphtho[1,2-c]pyrazole (m.p. 161°–163°C) or
q. 4,5-dihydro-3-(o-tolyl)-2H-naphtho[1,2-c]pyrazole (m.p. 186°–187°C) respectively.

When an equivalent amount of 2-bromo-benzo[b]cycloheptanone or 2-bromo-8-methoxy-benzo[b]cycloheptanone is substituted for the 2-bromo-α-tetralone in step A of example 1 above, there is obtained following the processes of steps A of example 1 and B above, 3-(4-pyridyl)-2,4,5,6-tetra-hydrobenzo[6,7]-cyclohepta[1,2-c]pyrazole(m.p. 217°–219°C) or 9-methoxy-3-(4-pyridyl)-2,4,5,6-tetrahydrobenzo[6,7-]cyclohepta [1,2-c]pyrazole (m.p. 200°–201°C) respectively.

EXAMPLE 13

When steps A and B of example 9 are carried out using equivalent amounts of 7,8-dimethoxy suberone and p-chlorobenzaldehyde in place of the benzosuberone and 4-pyridine-carboxaldehyde, there is obtained 8,9-dimethoxy-3-(p-chlorophenyl)-2,3,3a,4,5,6-hexahydrobenzo[6,7]cyclohepta[1,2-c]pyrazole (m.p. 160°–163°C).

The compounds of examples 2, 7 and 10 may be prepared by the processes of examples 3, 4, 5, 8, 9, 11 and 12 using equivalent amounts of appropriate starting materials and the compounds of example 9 may be prepared by the process of examples 1, 2, 3, 4, 5, 8, 10, 11 and 12 from equivalent amounts of appropriate starting materials.

What is claimed is:
1. A compound of the formula

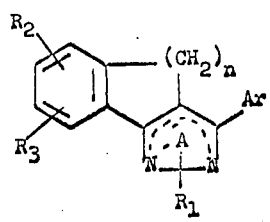

where ring A represents the structures

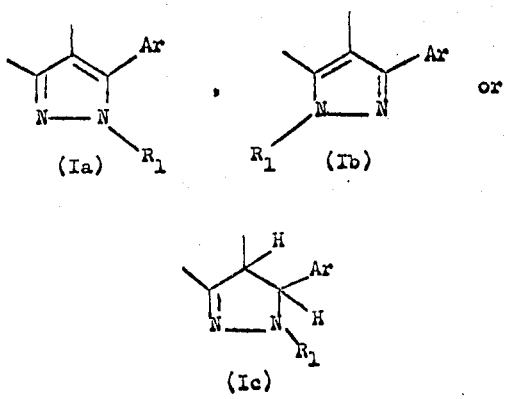

$n$ is 2;
$R_1$ represents hydrogen or lower alkyl having 1 to 4 carbon atoms excluding tertiary butyl;
Ar is

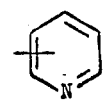

and
$R_2$ and $R_3$ each independently represent hydrogen, halo having an atomic weight of about 19 to 36, lower alkyl having 1 to 4 carbon atoms, lower alkoxy, trifluoromethyl or
$R_2$ and $R_3$ together independently represent methylenedioxy attached to adjacent carbon atoms,
provided that when $R_2$ and $R_3$ are independently trifluoromethyl or tertiary butyl they are not on adjacent carbon atoms, or a pharmaceutically acceptable acid addition salt thereof.

2. The compound of claim 1 having structure (1a) and (1b) when $R_1$ is hydrogen or structure (1b) when $R_1$ is lower alkyl.
3. The compound of claim 1, in which $R_1$ is hydrogen.
4. The compound of claim 3, in which $n$ is 2.
5. The compounds of claim 1 in which $R_1$ is hydrogen and Ar is pyridyl.
6. The compounds of claim 5 in which $n$ is 2.
7. The compound of claim 1 which is 4,5-dihydro-3-(4-pyridyl)-2H-naphtho[1,2-c]pyrazole.
8. The compound of claim 1 which is 4,5-dihydro-3-(2-pyridyl)-2H-naphtho[1,2-c]pyrazole.
9. The compound of claim 1 which is 4,5-dihydro-3-(3-pyridyl)-2H-naphtho[1,2-c]pyrazole.

* * * * *